(12) United States Patent
Hangauer et al.

(10) Patent No.: US 7,968,708 B2
(45) Date of Patent: Jun. 28, 2011

(54) AZEPANS AND METHODS FOR MAKING AND USING SAME

(75) Inventors: David G. Hangauer, East Amherst, NY (US); Fengzhi Li, Buffalo, NY (US); Taher Hegab, Fresno, CA (US); Xiang Ling, Snyder, NY (US)

(73) Assignees: The Research Foundation of State University of New York, Amherst, NY (US); Health Research Inc., Buffalo, NY (US)

( * ) Notice: Subject to any disclaimer, the term of this patent is extended or adjusted under 35 U.S.C. 154(b) by 511 days.

(21) Appl. No.: 11/999,723

(22) Filed: Dec. 6, 2007

(65) Prior Publication Data

US 2008/0161556 A1 Jul. 3, 2008

Related U.S. Application Data

(60) Provisional application No. 60/873,183, filed on Dec. 6, 2006.

(51) Int. Cl.
*C07D 401/04* (2006.01)
(52) U.S. Cl. ........................................................ 540/524
(58) Field of Classification Search .................. None
See application file for complete search history.

(56) References Cited

U.S. PATENT DOCUMENTS

| 5,532,359 A | 7/1996 | Marsters et al. |
| 5,843,941 A | 12/1998 | Marsters et al. |
| 5,916,888 A | 6/1999 | Peters et al. |
| 2004/0162426 A1 | 8/2004 | Lu et al. |

FOREIGN PATENT DOCUMENTS

| CA | 2162715 | 11/1994 |
| WO | WO 94/26718 | 11/1994 |
| WO | WO 2005/014574 | 2/2005 |

OTHER PUBLICATIONS

Owens et al. Bioorganic and Medicinal Chemistry Letters, 1998, 8(24), 3683-88.*
Flynn et al., "An Acyliminium Ion Route to Cis and Trans 'Anti' Phe-Gly Dipeptide Mimetics," *Bioorganic & Medicinal Chemistry Letters*, 1(6):309-312 (1991).
De Laszlo et al., "Synthesis and Use of 3-Amino-4-phenyl-2-piperidones and 4-Amino-2-benzazepin-3-ones as Conformationally Restricted Phenylalanine Isosteres in Renin Inhibitors," *Journal of Medicinal Chemistry*, 35(5):833-846 (1992).
Robl et al., "Peptidomimetic Synthesis: A Novel, Highly Stereoselective Route to Substituted Freidinger Lactams," *J. Am. Chem. Soc.*, 116:2348-2355 (1994).
Jalil et al., "Synthesis of the Precursor of Anti-Inflammatory Agents by Cross-Coupling Using Electrogenerated Highly Reactive Zinc," *Synthesis*, 2002:2681-2686 (2002).
Lawrence et al., "A Three-Component Coupling Process Based on Vicarious Nucleophilic Substitution (VNSAR)-Alkylation Reactions: An Approach to Indoprofen and Derivatives," *J. Org. Chem.*, 67(2):457-464 (2002).
Ballet et al., "Synthesis and Biological Evaluation of Constrained Analogues of the Opioid Peptide H-Tyr-d-Ala-Phe-Gly-NH2 Using the 4-Amino-2-benzazepin-3-one Scaffold," *Journal of Peptide Research*, 66(5):222-230(9) (2005).
Gu et al., "Parallel Synthesis and Biological Evaluation of Different Sizes of Bicyclo[2,3]-Leu-Enkephalin Analogues," *Biopolymers*, 80(2-3):151-163 (2005).
Ling et al., "Differential Expression of Survivin-2B and Survivin-DeltaEx3 Is Inversely Associated with Disease Relapse and Patient Survival in Non-Small-Cell Lung Cancer (NSCLC)," *Lung Cancer*, 49:353-361 (2005).
Van Rompaey, et al., "Synthesis and Evaluation of the beta-Turn Properties of 4-Amino-1,2,4,5-tetrahydro-2-benzazepin-3-ones and of Their Spirocyclic Derivative," *European Journal of Organic Chemistry*, 2006(13):2899-2911 (2006).

* cited by examiner

*Primary Examiner* — Noble Jarrell
(74) *Attorney, Agent, or Firm* — Hodgson Russ LLP

(57) ABSTRACT

Disclosed are compounds having the formula:

wherein $Z^1$ is an alkylene moiety; Q is a carboxylic acid derivative; and $R^1$ and $R^2$ are the same or different and are selected from the group consisting of alkyl, aryl, alkylcarbonyl, arylcarbonyl, hydroxycarbonyl, and alkoxycarbonyl or $R^1$ and $R^2$, taken together with the nitrogen atom to which they are bound, form a ring. Also disclosed are compounds having the formula:

wherein $Z^1$ is an alkylene moiety; Q is a carboxylic acid derivative; and $R^{13}$ is selected from the group consisting of alkyl and aryl. The compounds can be used to modulate cell proliferation and/or apoptosis, for example, in the treatment of cancers and other proliferative diseases, disorders, and conditions.

8 Claims, 7 Drawing Sheets

AZEPANS AND METHODS FOR MAKING AND USING SAME

The present application claims the benefit of U.S. Provisional Patent Application Ser. No. 60/873,183, filed Dec. 6, 2006, which provisional patent application is hereby incorporated by reference.

FIELD OF THE INVENTION

The present invention relates generally to azepans and, more particularly, to 2-oxo-azepans that are substituted in the 1- and 3-positions.

BACKGROUND OF THE INVENTION

Normal tissues in the body are formed either by cells that have reached a terminally differentiated state and no longer divide or by cells that die after a period of time and are replaced from a pool of dividing cells. For example, nervous tissue is formed early in development and the cells of the nervous system reach a terminally differentiated state soon after birth. In contrast, the body has a number of self renewing tissues such as skin, gut, bone marrow and sex organs which undergo a balanced flux of cell birth and death. This flux, which results in the production of 50 to 70 billion cells per day in an average adult and amounting to a mass of cells equivalent to an entire body weight over a years time, is balanced by the regulated eradication of an equivalent number of cells. In self-renewing tissues the eradication is maintained, in part, due to the process of programmed cell death, known as apoptosis, in which the cells are genetically "programmed" to die after a certain period of time.

Apoptosis is particularly prominent during the development of an organism, where cells that perform transitory functions are programmed to die after their function no longer is required. In addition, apoptosis can occur in cells that have undergone major genetic alterations, thus providing the organism with a means to rid itself of defective and potentially cancer forming cells. Apoptosis also can be induced due to exposure of an organism to various external stimuli, including, for example, bacterial toxins, ethanol, and ultraviolet radiation. Chemotherapeutic agents for treating cancer also are potent inducers of apoptosis.

The regulation of programmed cell death is a complex process involving numerous pathways and, on occasion, defects occur in the regulation of programmed cell death. Given the critical role of this process in maintaining a steady-state number of cells in a tissue or in maintaining the appropriate cells during development of an organism, defects in programmed cell death often are associated with pathologic conditions. It is estimated that either too little or too much cell death is involved in over half of the diseases for which adequate therapies do not currently exist.

Various disease states occur due to aberrant regulation of programmed cell death in an organism. For example, defects that result in a decreased level of apoptosis in a tissue as compared to the normal level required to maintain the steady-state of the tissue can result in an increased number of cells in the tissue. Such a mechanism of increasing cell numbers has been identified in various cancers, where the formation of a tumor occurs not because the cancer cells necessarily are dividing more rapidly than their normal counterparts, but because the cells are not dying at their normal rate.

For these and other reasons, a need exists for agents capable of modulating programmed cell death pathways. The present invention is directed, in part, to addressing this need.

SUMMARY OF THE INVENTION

The present invention relates to a compound having the formula:

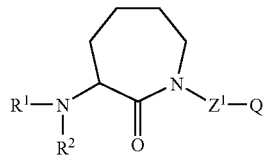

wherein $Z^1$ is an alkylene moiety; Q is a carboxylic acid derivative; and $R^1$ and $R^2$ are the same or different and are selected from the group consisting of alkyl, aryl, alkylcarbonyl, arylcarbonyl, hydroxycarbonyl, and alkoxycarbonyl or $R^1$ and $R^2$, taken together with the nitrogen atom to which they are bound, form a ring.

The present invention relates to a compound having the formula:

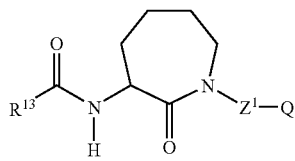

wherein $Z^1$ is an alkylene moiety; Q is a carboxylic acid derivative; and $R^{13}$ is selected from the group consisting of alkyl and aryl.

BRIEF DESCRIPTION OF THE DRAWINGS

FIGS. 5C-5E are images of MCF-7 breast cancer cells after 3 days' treatment with 20 μM of a compound of the present invention, and FIGS. 5A-5B are control images (no compound of the present invention).

DETAILED DESCRIPTION OF THE INVENTION

Figure 1A:
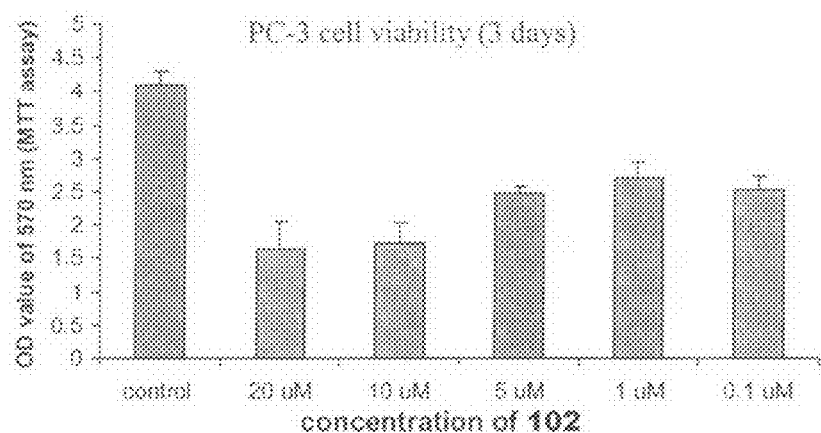
FIGS. 1A-1B are bar graphs showing the effect of a compound of the present invention on PC-3 prostate cancer cell growth inhibition after 3 days treatment (FIG. 1A) and 5 days treatment (FIG. 1B).

As used herein, "alkyl" is meant to include linear alkyls, branched alkyls, and cycloalkyls, each of which can be substituted or unsubstituted. "Alkyl" is also meant to include lower linear alkyls (e.g., C1-C6 linear alkyls), such as methyl, ethyl, n-propyl, n-butyl, n-pentyl, and n-hexyl; lower branched alkyls (e.g., C3-C8 branched alkyls), such as isopropyl, t-butyl, 1-methylpropyl, 2-methylpropyl, 1-methylbutyl, 2-methylbutyl, 3-methylbutyl, 1,2-dimethylpropyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 2-methyl-2-ethylpropyl, 2-methyl-1-ethylpropyl, and the like; and lower cycloalkyls (e.g., C3-C8 cycloalkyls), such as cyclopropyl, cyclobutyl, cyclopentyl, cyclohexyl, and the like. "Alkyl", as used herein, is meant to include unsubstituted alkyls, such as those set forth above, in which no atoms other than carbon and hydrogen are present. "Alkyl", as used herein, is also meant to include substituted alkyls. Suitable substituents include aryl groups (which may themselves be substituted), heterocyclic rings (saturated or unsaturated and optionally substituted), alkoxy groups (which is meant to include aryloxy groups (e.g., phenoxy groups)), amine groups (e.g., disubstituted with aryl or alkyl groups), carboxylic acid derivatives (e.g., carboxylic acid esters, amides, etc.), halogen atoms (e.g., Cl, Br, and I), and the like. Further, alkyl groups bearing one or more alkenyl or alkynyl substituents (e.g., a methyl group itself substituted with a prop-1-en-1-yl group to produce a but-2-en-1-yl substituent) is meant to be included in the meaning of "alkyl". Other suitable substituents include hydroxy groups and protected hydroxy groups (e.g., an acyloxy group, such as an acetoxy group; a silyl ether group, such as a trimethylsilyl ("TMS") ether group and a tert-butyldimethylsilyl ("TBS") ether group).

As used herein, "alkylene" refers to a bivalent alkyl group, where alkyl has the meaning given above. Linear, branched, and cyclic alkylenes, as well as examples thereof, are defined in similar fashion with reference to their corresponding alkyl group. Examples of alkylenes include eth-1,1-diyl (i.e., —CH(CH$_3$)—), eth-1,2-diyl (i.e., —CH$_2$CH$_2$—), prop-1,1-diyl (i.e., —CH(CH$_2$CH$_3$)—), prop-1,2-diyl (i.e., —CH$_2$—CH(CH$_3$)—), prop-1,3-diyl (i.e., —CH$_2$CH$_2$CH$_2$—), prop-2,2-diyl (e.g. —C(CH$_3$)$_2$—), cycloprop-1,1-diyl, cycloprop-1,2-diyl, cyclopent-1,1-diyl, cyclopent-1,2-diyl, cyclopent-1,3-diyl, cyclohex-1,1-diyl, cyclohex-1,2-diyl, cyclohex-1,3-diyl, cyclohex-1,4-diyl, but-2-en-1,1-diyl, cyclohex-1,3-diyl, but-2-en-1,4-diyl, but-2-en-1,2-diyl, but-2-en-1,3-diyl, but-2-en-2,3-diyl. Also included in the meaning of the term "alkylene" are compounds having the formula —R'—R"—, where —R' represents a linear or branched alkyl group and R"— represents a cycloalkyl group.

As used herein, "alkoxy" is meant to include groups having the formula —O—R, where R is an alkyl or aryl group. They include methoxy, ethoxy, propoxy, phenoxy, 4-methylphenoxy, and the like.

As used herein, "aryl" is meant to include aromatic rings, for example, aromatic rings having from 4 to 12 members, such as phenyl rings. These aromatic rings can optionally contain one or more heteroatoms (e.g., one or more of N, O, and S), and, thus, "aryl", as used herein, is meant to include heteroaryl moieties, such as pyridyl rings, pyridiminyl rings, and furanyl rings. The aromatic rings can be optionally substituted. "Aryl" is also meant to include aromatic rings to which are fused one or more other aryl rings or non-aryl rings. For example, naphthyl groups, indole groups, isoindole groups, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), alkoxy groups (which is meant to include aryloxy groups (e.g., phenoxy groups)), amine groups (e.g., disubstituted with aryl or alkyl groups), carboxylic acid groups, carboxylic acid derivatives (e.g., carboxylic acid esters, amides, etc.), halogen atoms (e.g., Cl, Br, and I), and the like.

As used herein, "ring" is meant to include homocyclic or heterocyclic rings. The homocyclic or heterocyclic ring can be saturated or unsaturated, aromatic or non-aromatic. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems, and such fused ring systems can be saturated or unsaturated, aromatic or non-aromatic. In the case where the ring is saturated (i.e., in the case where each of the atoms making up the ring are joined by single bonds to other members of the ring), the ring may optionally include unsaturated (aromatic or nonaromatic) or saturated substituents. Illustratively, the ring or ring system can contain 3, 4, 5, 6, 7, 8, 9, 10, or more members.

As used herein, "carboxylic acid derivative" is meant to include free carboxylic acids, carboxylic acid salts, carboxylic acid esters, carboxylic acid amides, carboxylic acid chlorides and other carboxylic acid halides.

As used herein, "alkylcarbonyl", "arylcarbonyl", "hydroxycarbonyl", and "alkoxycarbonyl" are meant to refer to moieties which have the following formulae: —C(O)-alkyl, —C(O)-aryl, —C(O)-hydroxy, and —C(O)-alkoxy, respectively, wherein C(O) represents a carbonyl (C=O) group.

The present invention, in one aspect thereof, relates to a compound having the formula:

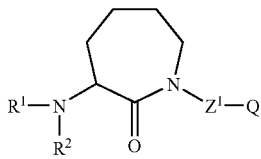

wherein $Z^1$ is an alkylene moiety; Q is a carboxylic acid derivative; and $R^1$ and $R^2$ are the same or different and are selected from the group consisting of alkyl, aryl, alkylcarbonyl, arylcarbonyl, hydroxycarbonyl, and alkoxycarbonyl or $R^1$ and $R^2$, taken together with the nitrogen atom to which they are bound, form a ring.

As noted above, $Z^1$ is an alkylene moiety, examples of which include methylene moieties, ethylene moieties, n-propylene moieties, n-butylene moieties, and the like. These alkylene moieties can be substituted or unsubstituted. Suitable substituents include, for example, other alkyl groups (which can themselves be substituted, with, for example, aryl groups, as in the case where the alkylene moiety is substituted with a benzyl or other aralkyl group. Illustratively, $Z^1$ can have the formula $-(CH_2)_n$- where n is an integer from 1 to 8, such as in the case where n is an integer from 1 to 6, an integer from 1 to 4, 1, 2, 3, 4, 5, 6, 7, 8, etc. Illustratively, $Z^1$ can be a methylene, ethylene, n-propylene, n-butylene, or other alkylene moiety bearing one, two or three substituents, such as in the case where $Z^1$ is a methylene, ethylene, n-propylene, n-butylene, or other alkylene moiety bearing exactly one substituent (e.g., an arylmethyl substituent or other aralkyl substituent), for example, on the carbon immediately adjacent to the azepan ring's nitrogen or on the carbon immediately adjacent to the carboxylic acid derivative. In certain embodiments, $Z^1$ is a methylene moiety, such as in the case where $Z^1$ has the formula —CH($R^6$)— or —C($R^6$)($R^{20}$)— in which $R^6$ and $R^{20}$ are the same or different and are selected from alkyl groups and aryl groups, for example, as in the case where $Z^1$ has the formula —CH($R^6$)— in which $R^6$ is an alkyl group (e.g., a benzyl group or other aralkyl group).

In certain embodiments, Q is an amide. The amide nitrogen can be unsubstituted, monosubstituted, or disubstituted. Illustratively, the amide nitrogen can be substituted with one alkyl group, with two alkyl groups (which can be the same or different), with one aryl group, with two aryl groups (which can be the same or different), or with one alkyl group and one aryl group; or the amide nitrogen can be incorporated into a ring (e.g., a 4- to 8-membered ring). In certain embodiments Q has the formula —C(O)—N($R^4$)($R^5$) in which $R^4$ and $R^5$ are the same or different and are selected from the group consisting of hydrogen, alkyl, and aryl or in which $R^4$ and $R^5$, taken together with the nitrogen atom to which they are bound, form a ring, such as a 5- or 6-membered ring).

In certain embodiments, the compound of the present invention has the formula:

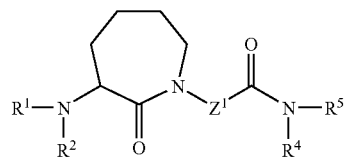

in which $Z^1$ is an alkylene moiety (e.g., any of the alkylene moieties discussed above) and in which $R^4$ and $R^5$ are the same or different and are selected from the group consisting of hydrogen, alkyl, and aryl or in which $R^4$ and $R^5$, taken together with the nitrogen atom to which they are bound, form a ring. Illustratively, $R^4$ can be a hydrogen, and $R^5$ can be an alkyl group (e.g., a benzyl group or other aralkyl group which can be optionally substituted, for example, with substituents containing one or more groups which increase the compound's water solubility, such as morpholino groups, piperazine groups, acid groups (e.g., carboxylic acid groups), polyethers, etc.).

Illustratively, the compound of the present invention can have the formula:

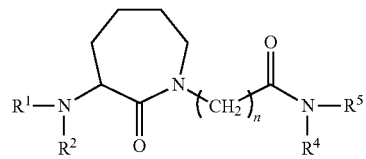

in which $R^4$ and $R^5$ are the same or different and are selected from the group consisting of hydrogen, alkyl, and aryl or in which $R^4$ and $R^5$, taken together with the nitrogen atom to which they are bound, form a ring (for example, as discussed above) and in which n is an integer from 1 to 4. By way of further illustration, such compounds can have the formula:

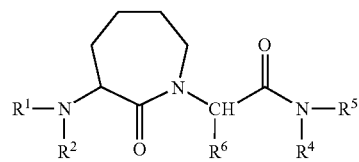

in which $R^6$ is an alkyl group, such as an aralkyl group (e.g., a benzyl group or other arylmethyl group). By way of still further illustration, such compounds can have the formula:

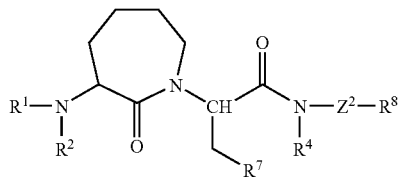

in which $R^7$ is an aryl group; $R^8$ is an aryl group; and $Z^2$ represents an alkylene moiety (suitable examples of which include those discussed above in the context of $Z^1$). By way of still further illustration, such compounds can have the formula:

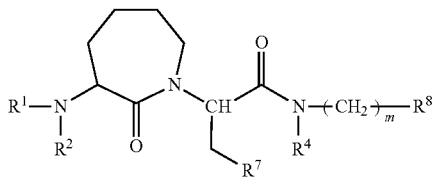

in which $R^7$ is an aryl group; $R^8$ is an aryl group; and m is 0, 1, 2, or 3. In certain embodiments, $R^7$ is a phenyl group; in certain embodiments, $R^8$ is a phenyl group; in certain embodiments, both $R^7$ and $R^8$ are phenyl groups; in certain embodiments, both $R^7$ and $R^8$ are phenyl groups, and $R^4$ is a hydrogen atom. In cases where both $R^7$ and $R^8$ are phenyl groups, these phenyl groups can be the same or they can be different. Examples of suitable phenyl groups include unsubstituted phenyl group as well as phenyl group substituted in one, two, or more positions. Illustratively, $R^8$ can be a phenyl group that is substituted (e.g., mono- or di-substituted in the ortho and/or para positions) with one or more groups that increase the compound's water solubility, such as morpholino-containing groups, piperazine-containing groups, acid-containing groups (e.g., carboxylic acid-containing groups), polyether-containing groups, etc.), examples of which include groups having the formula —O—$Z^3$—$R^{22}$, in which $Z^3$ represents an alkylene moiety (such as those discussed hereinabove) and in which $R^{22}$ represents a morpholino group, piperazine group, carboxylic acid or other acid, polyether group, etc.).

In each of the above formulae, $R^1$ and $R^2$ can be the same or different, and they are selected from the group consisting of alkyl, aryl, alkylcarbonyl, arylcarbonyl, hydroxycarbonyl, and alkoxycarbonyl or $R^1$ and $R^2$, taken together with the nitrogen atom to which they are bound, form a ring.

In certain embodiments, $R^1$ is an alkylcarbonyl, an arylcarbonyl, a hydroxycarbonyl, or an alkoxycarbonyl, such as in the case where the compound of the present has the following formula:

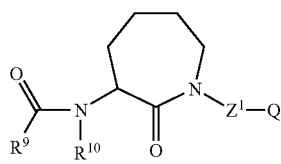

wherein $R^9$ is selected from the group consisting of alkyl, aryl, alkoxy and hydroxy, and $R^{10}$ is selected from the group consisting of alkyl and aryl; or $R^9$ and $R^{10}$, taken together with the atoms to which they are bound, form a ring. In certain embodiments, $R^9$ is an alkyl, such as an alkyl having the formula —CH(NR$^{24}$R$^{25}$)R$^{26}$ wherein $R^{24}$ and $R^{25}$ are the same or different and are selected from the group consisting of hydrogen, alkyl, and aryl and $R^{26}$ is selected from the group consisting of hydrogen, alkyl, and aryl (e.g., as in the case where $R^{24}$ is H, $R^{25}$ is H, and $R^{26}$ is an alkyl (e.g., a methyl, ethyl, propyl, or butyl group, such a group having the formula —CH$_3$ or —CH$_2$CH$_3$). In certain embodiments, $R^9$ and $R^{10}$, taken together with the atoms to which they are bound, form a 5- to 10-membered ring, such as 5-membered or 6-membered ring (e.g., a 5- or 6-membered ring bearing a double-bonded oxygen on one of the carbon atoms adjacent to the nitrogen to which $R^{10}$ is bonded, which 5- or 6-membered ring can be optionally have an aryl ring fused thereto. In certain embodiments, $R^9$ and $R^{10}$, taken together with the atoms to which they are bound, form an indolyl or isoindolyl ring (e.g., a 1-oxo-1,3-dihydro-isoindol-2-yl ring, which ring may be optionally substituted). In certain embodiments, $R^9$ and $R^{10}$ are selected such that compounds of the present invention have the formula:

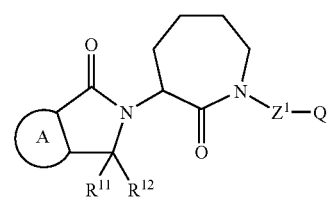

wherein $R^{11}$ and $R^{12}$ are the same or different and are selected from the group consisting of hydrogen, alkyl, and aryl; and wherein A represents a fused aryl ring (e.g., a phenyl, a naphthyl, a pyridyl, etc.). Illustratively, suitable fused aryl rings include unsubstituted phenyl rings, mono-substituted phenyl rings, disubstituted phenyl rings, unsubstituted naphthyl rings, mono-substituted naphthyl rings, disubstituted naphthyl rings, unsubstituted pyridyl rings, mono-substituted pyridyl rings, disubstituted pyridyl rings, etc. In certain embodiments, $R^{11}$ is a hydrogen atom; in certain embodiments, both $R^{11}$ and $R^{12}$ are hydrogen atoms; in certain embodiments, both $R^{11}$ and $R^{12}$ are hydrogen atoms and A represents a phenyl ring; and in certain embodiments, both $R^{11}$ and $R^{12}$ are hydrogen atoms and A represents an unsubstituted phenyl ring.

Illustratively, compounds of the present invention include those having the following formula:

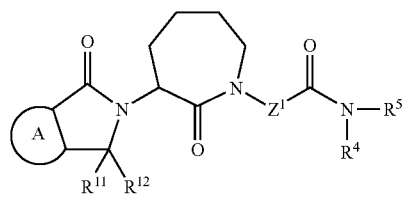

as well as those having the following formula:

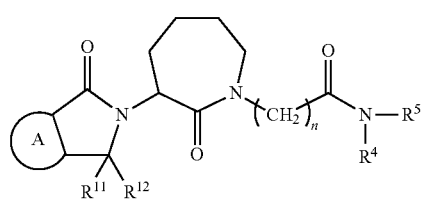

and those having the following formula:

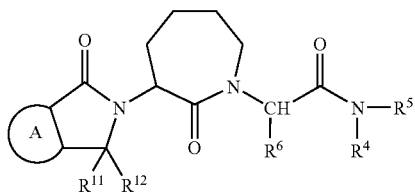

wherein A, $R^{11}$, $R^{12}$, $Z^1$, n, $R^4$, $R^5$, and $R^6$ have the meanings set forth above. Suitable examples of A, $R^{11}$, $R^{12}$, n, $R^4$, $R^5$ and $R^6$ include those set forth above. For example, in certain embodiments, A is a phenyl group (e.g., an unsubstituted phenyl group); each of $R^{11}$ and $R^{12}$ is a hydrogen atom; and/or $R^6$ is an aralkyl group (e.g., a benzyl group or a different arylmethyl group).

By way of further illustration, compounds of the present invention include those having the following formula:

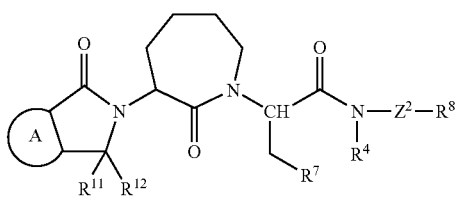

as well as those having the following formula:

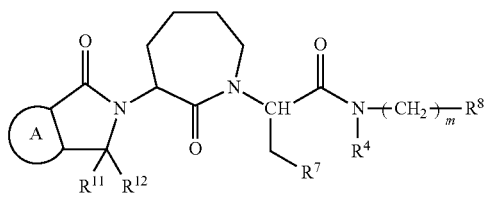

wherein A, $R^{11}$, $R^{12}$, $R^4$, $R^7$, $R^8$, m, and $Z^2$ have the meanings set forth above. Suitable examples of A, $R^{11}$, $R^{12}$, $R^4$, $R^7$, $R^8$, m, and $Z^2$ include those set forth above. For example, in certain embodiments, A is a phenyl group (e.g., an unsubstituted phenyl group); each of $R^{11}$ and $R^{12}$ is a hydrogen atom; m is 1; $R^4$ is an hydrogen atom; $R^7$ is a phenyl group (e.g., an unsubstituted phenyl group); and/or $R^8$ is a phenyl group (e.g., an unsubstituted phenyl group).

By way of still further illustration, compounds of the present invention include those having the following formula:

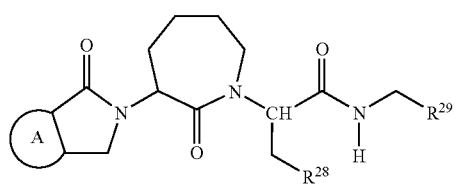

wherein A is a fused aryl group (suitable examples of which are discussed above), and wherein $R^{28}$ and $R^{29}$ are the same or different aryl groups (e.g., substituted or unsubstituted phenyl groups), such as in the case where the compound has the following formula:

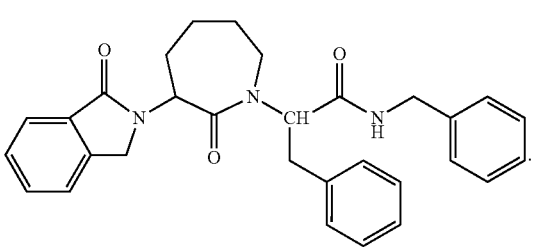

The present invention, in another aspect thereof, relates to compounds having the formula:

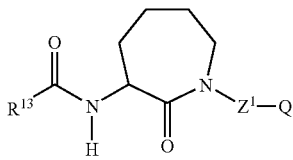

wherein $Z^1$ is an alkylene moiety; Q is a carboxylic acid derivative; and $R^{13}$ is selected from the group consisting of alkyl and aryl.

Examples of suitable $Z^1$ alkylene moieties include those discussed above. For example, $Z^1$ can have the formula $-(CH_2)_n$ in which n is an integer from 1 to 4. Illustratively, Q can be an amide, suitable examples of which include those discussed above.

In certain embodiments, the compound has the following formula:

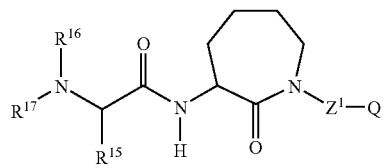

wherein $R^{15}$, $R^{16}$, and $R^{17}$ are the same or different and are selected from the group consisting of hydrogen, alkyl, and aryl or in which two or more of $R^{15}$, $R^{16}$, and $R^{17}$ combine to form a ring. For example, in certain embodiments, $R^{15}$, $R^{16}$, and $R^{17}$ are the same or different and are selected from the group consisting of hydrogen, alkyl, and aryl; in certain embodiments, $R^{15}$ is a hydrogen, alkyl, or aryl, and $R^{16}$ and $R^{17}$ combine to form a ring; and, in certain embodiments, $R^{16}$ is a hydrogen, alkyl, or aryl, and $R^{15}$ and $R^{17}$ combine to form a ring.

By way of illustration, $R^{15}$ can be an alkyl, for example, a methyl, ethyl, propyl, or butyl group, such a group having the formula $-CH_3$ or $-CH_2CH_3$. In certain embodiments, $R^{15}$ is an ethyl group, such as a substituted ethyl group (e.g., a mono-substituted, di-substituted, or tri-substituted ethyl group) or an unsubstituted ethyl group (having the formula $-CH_2CH_3$). In certain embodiments, $R^{15}$ is an ethyl group (such as those described above) and each of $R^{16}$ and $R^{17}$ is a hydrogen atom.

Illustratively, compounds of the present invention include those having the following formula:

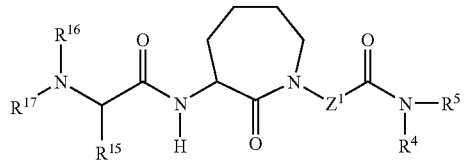

as well as those having the following formula:

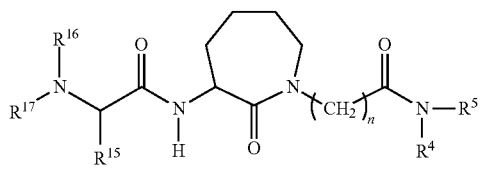

and those having the following formula:

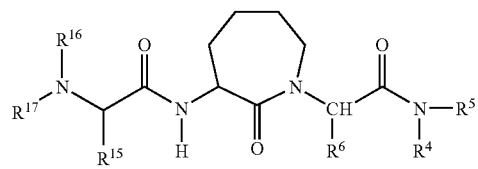

wherein $R^{15}$, $R^{16}$, $R^{17}$, $Z^1$, n, $R^4$, $R^5$, and $R^6$ have the meanings set forth above. Suitable examples of $R^{15}$, $R^{16}$, $R^{17}$, $Z^1$, n, $R^4$, $R^5$, and $R^6$ include those set forth above. For example, in certain embodiments, $R^{15}$ is an alkyl (e.g., a methyl, ethyl, propyl, or butyl group); and/or each of $R^{16}$ and $R^{17}$ is a hydrogen atom.

By way of further illustration, compounds of the present invention include those having the following formula:

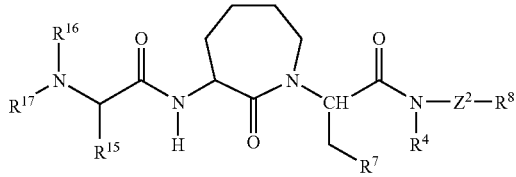

as well as those having the following formula:

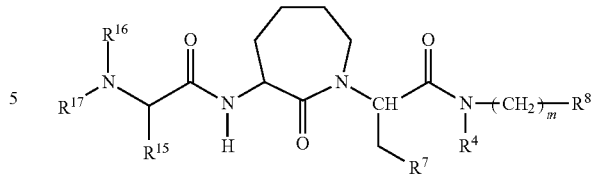

wherein $R^{15}$, $R^{16}$, $R^{17}$, $R^4$, $R^7$, $R^8$, m, and $Z^2$ have the meanings set forth above. Suitable examples of $R^{15}$, $R^{16}$, $R^{17}$, $R^4$, $R^7$, $R^8$, m, and $Z^2$ include those set forth above. For example, in certain embodiments, $R^{15}$ is an alkyl (e.g., a methyl, ethyl, propyl, or butyl group); each of $R^{16}$ and $R^{17}$ is a hydrogen atom; m is 1; $R^4$ is an hydrogen atom; $R^7$ is a phenyl group (e.g., an unsubstituted phenyl group); and/or $R^8$ is a phenyl group (e.g., an unsubstituted phenyl group).

By way of still further illustration, compounds of the present invention include those having the following formula:

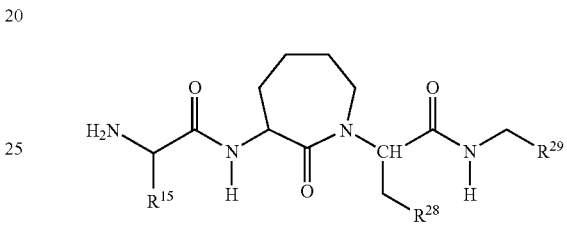

$R^{15}$ is an alkyl group) (suitable examples of which are discussed above), and wherein $R^{28}$ and $R^{29}$ are the same or different aryl groups (e.g., substituted or unsubstituted phenyl groups), such as in the case where the compound has the following formula:

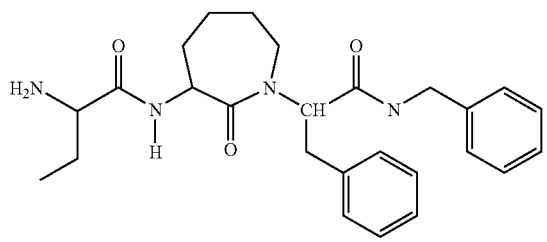

The aforementioned compounds of the present invention can be prepared by any suitable method, for example, by the methods described below, to which methods the present invention also relates.

For example, compounds of the present invention can be made by a procedure according to Scheme 1.

SCHEME 1

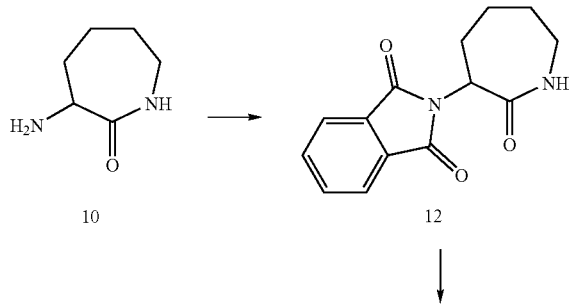

-continued

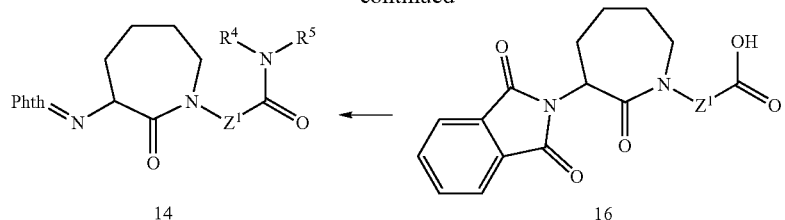

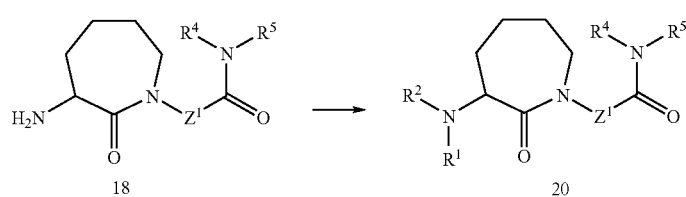

Briefly, phthalimide 12 can be prepared from commercially available aminocaprolactam 10, for example, by reaction of 10 with phthalic anhydride. Phthalimide 12 can then be alkylated with a halogenated acid ester (such as Br—$Z^1$—COOR$^{30}$ or I—$Z^1$—COOR$^{30}$, where R$^{30}$ is, for example, alkyl or aryl, such as in the case where R$^{30}$ is an ethyl group) followed by hydrolysis to obtain acid 14. Acid 14 can then be coupled with various amines to form amide 16. The phthalyl group can then be removed to form amine 18, and amine 18 can be alkylated to produce compound 20 (a compound of the present invention).

Certain compounds of the present invention can be produced by other, perhaps more efficient methods.

For example, Scheme 2 shows a method for making a compound 22.

SCHEME 2

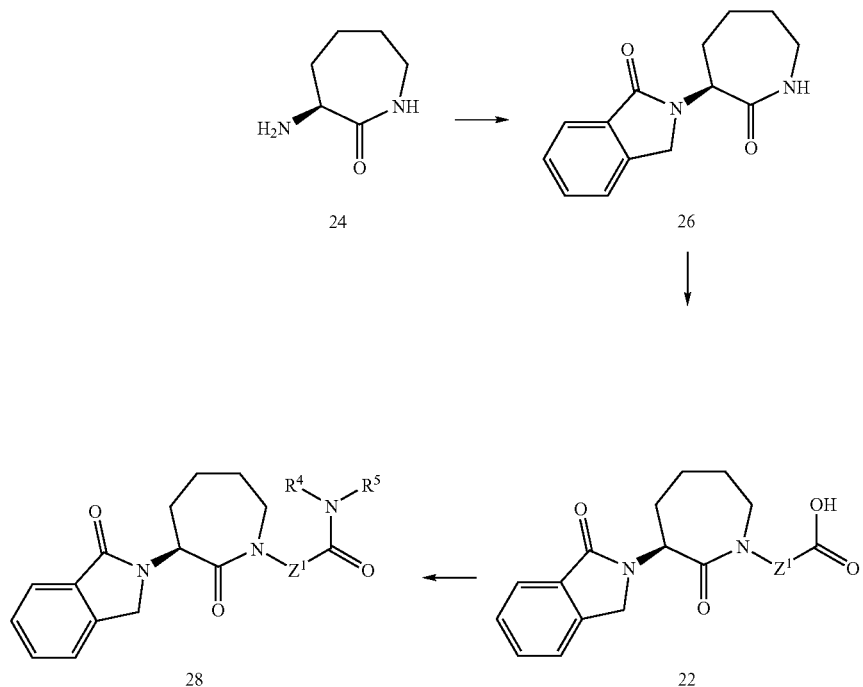

Briefly, referring to Scheme 2, aminocaprolactam 24 is converted to isoindole 26, using for example, the methodologies set forth in Jalil et al., "Synthesis of the Precursor of Anti-Inflammatory Agents by Cross-Coupling Using Electrogenerated Highly Reactive Zinc," *Synthesis*, 2002:2681-2686; and Lawrence et al., "A Three-Component Coupling Process Based on Vicarious Nucleophilic Substitution (VNSAR)-Alkylation Reactions: An Approach to Indoprofen and Derivatives," *J. Org. Chem.*, 67(2):457-464 (2002), which are hereby incorporated by reference. Isoindole 26 can then be alkylated with a halogenated acid ester (such as Br—$Z^1$—$COOR^{31}$ or I—$Z^1$—$COOR^{31}$, where $R^{31}$ is, for example, alkyl or aryl, such as in the case where $R^{31}$ is an ethyl group) followed by hydrolysis to obtain acid 28. Acid 28 can then be coupled with various amines to form compound 22. As one will appreciate, the nature of the halogenated acid ester employed in the conversion of 26 to 28 will depend on the desired identity of $Z^1$ in compound 22. For example, in cases where $Z^1$ is a —$CH_2$— group, an alkyl bromoacetate can be employed in the conversion of 26 to 28.

By way of further illustration, Scheme 3 shows a method for making a compound 32.

For example, compounds of the present invention in which Q is an amide can be used to modulate cell proliferation and/or apoptosis, and are believed to be particularly useful in the treatment of proliferative diseases, disorders, and/or conditions, such as prostate, colon, ovarian, lung, breast, and other cancers.

In one aspect, compounds of the present invention can be used to decrease proliferation of cancer cells. In another aspect, compounds of the present invention can be used to induce apoptosis of cancer cells. The method includes contacting a sample which includes cancer cells with a compound of the present invention. The meaning of the terms "proliferation" and "apoptosis" are readily understood in the art. Illustrative methods for assaying for proliferation and apoptosis are provided in the examples which follow. "Cancer cells", as used herein, are meant to include cancerous epithelial cells, such as prostate cancer cells, lung cancer cells, breast cancer cells, ovarian cancer cells, and colon cancer cells. The methods of the present invention can be practiced in vitro or in vivo.

For example, the method of the present invention can be used in vivo to treat cancers, such as prostate cancer, lung

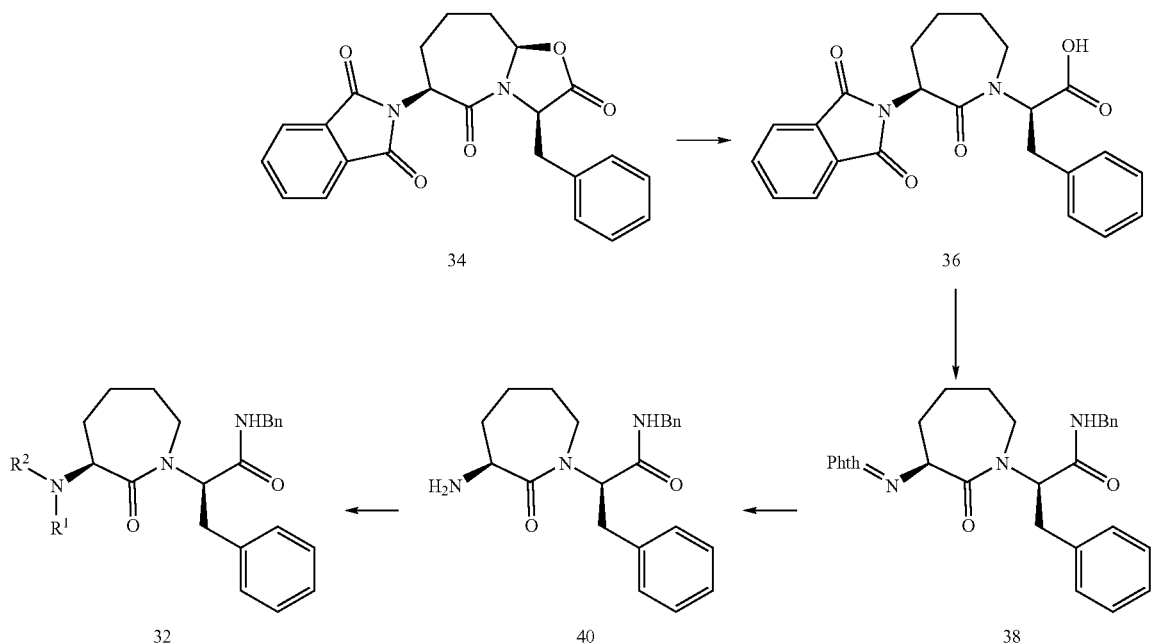

SCHEME 3

Briefly, referring to Scheme 3, acid 36 can be prepared from compound 34 using, for example, the methodologies described in Robl et al., "Peptidomimetic Synthesis: A Novel, Highly Stereoselective Route to Substituted Freidinger Lactams," *J. Am. Chem. Soc.*, 116:2348-2355 (1994), which is hereby incorporated by reference. Acid 36 can then be coupled to benzyl amine (or, more generically, to other amines, such as those having the formula $HNR^4R^5$, in which case the —NHBn group in Scheme 3 would be replaced with the more generic —$NR^4R^5$) to form amide 38. The phthalyl group can then be removed to form amine 40, and amine 40 can be alkylated to produce compound 32.

The compounds of the present invention and compounds produced by the methods of the present invention can be used in a variety of ways.

cancer, ovarian cancer, breast cancer, and colon cancer. In the case where the method of the present invention is carried out in vivo, for example, where the cancer cells are present in a human subject, contacting can be carried out by administering a therapeutically effective amount of a compound in accordance with the present invention to the human subject, for example, by directly injecting a compound of the present invention into a tumor. Details with regard to administering the compounds are described below.

The compounds of the present invention can also be used in a method for treating cancer, such as prostate cancer, lung cancer, breast, ovarian cancer, colon cancer, or other cancers. As used in the context of this aspect of the present invention, "treating" is meant to include preventative treatments, for example in a subject at risk for cancer, as well as treatments designed to slow, stop, or reverse progression of the cancer in subjects exhibiting clinical symptoms of cancer. The method includes administering, to the subject, a compound in accordance with the present invention.

Suitable subjects include, for example mammals, such as rats, mice, cats, dogs, horses, monkeys, and humans. Suitable human subjects include, for example, those which have previously been determined to be at risk of having prostate cancer, lung cancer, ovarian cancer, colon cancer, and/or breast cancer and those who have been diagnosed as having such cancers. Preferably, the subject suffers from only one of these types of cancers.

In subjects who are determined to be at risk of having cancer, the above-identified compounds are administered to the subject, preferably under conditions effective to decrease proliferation and/or induce apoptosis of the cancer cells in the event that they develop. Such preventive (which is not used in the absolute 100% sense) therapy can be useful in high risk individuals as long as the adverse side effects of the administration of these compounds are outweighed by the potential benefit of prevention.

It should be noted that the above-described methods for treating cancer may operate via a mechanism which involves inducing caspase activation (e.g., inducing caspase 3 and/or caspase 9 activation), inhibiting colony formation, downregulating survivin expression and promoter activity, arresting cancer cells in the G1 phase of the cell cycle, inhibition of Bcl-2 expression, inducing DNA fragmentation. However, such need not be the case, and this aspect of the present invention is not, in any way, intended to be limited by the mechanism by which the compounds of the present invention operate.

Any of the compounds of the present invention described above can be used in the treatment methods of the present invention. The compounds may be administered alone or in combination with compatible carriers as a composition. Compatible carriers include suitable pharmaceutical carriers or diluents. The diluent or carrier ingredients should be selected so that they do not diminish the therapeutic effects of the compound.

The compositions herein may be made up in any suitable form appropriate for the desired use. Examples of suitable dosage forms include oral, parenteral, or topical dosage forms.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, such as ethyl-p-hydroxybenzoate. Dosage forms for oral administration can also be formulated as food preparations using materials which are conventionally used in the food processing industry, such as proteins, sugars and other carbohydrates, extenders, fillers, preservatives, and the like.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

Suitable topical dosage forms include gels, creams, lotions, ointments, powders, aerosols and other conventional forms suitable for direct application of medicaments to skin or mucous membranes. Topical ointments, pastes, creams, and gels can include, in addition to the active compounds of the present invention, customary excipients, for example animal and vegetable fats, waxes, paraffins, starch, tragacanth, cellulose derivatives, polyethylene glycols, silicones, bentonites, silicic acid, talc, and zinc oxide, or mixtures of these substances. Topical powders and sprays can include, in addition to the active compounds of the present invention, the customary excipients, for example lactose, talc, silicic acid, aluminium hydroxide, calcium silicate and polyamide powder, or mixtures of these substances. Sprays can additionally contain the conventional propellants, such as chlorofluorohydro-carbons.

In addition to the above, generally non-active components of the above-described formulations, these formulations can include other active materials, particularly, actives which have been identified as useful in the treatment of prostate, lung, breast, colon, ovarian cancers and/or other cancers. These actives can be broad-based anti-cancer agents, such that they also are useful in treating other types of cancers or they may be more specific, for example, in the case where the other active is useful for treating particular types of adenocarcinomas. The other actives can also have non-anti-cancer pharmacological properties in addition to their anti-cancer properties. For example, the other actives can be XIAP antagonists; they can be inhibitors of XIAP expression; and/or they can have anti-inflammatory properties. Alternatively, the other actives can have none of these properties.

It will be appreciated that the actual preferred amount of compound of the present invention to be administered will vary according to the particular compound being used, the particular composition formulated, and the mode of administration. Many factors that may modify the action of the compound (e.g., body weight, sex, diet, time of administration, route of administration, rate of excretion, condition of the subject, drug combinations, and reaction sensitivities and severities) can be taken into account by those skilled in the art. Administration can be carried out continuously or periodically within the maximum tolerated dose. Optimal administration rates for a given set of conditions can be ascertained by those skilled in the art using conventional dosage administration tests.

It will be appreciated that certain compounds of the present invention may be more suitable for in vivo use than others. Illustratively, compounds of the present invention in which Q is a free carboxylic acid or a carboxylic acid halide may have minimal use in vivo, and compounds of the present invention in which Q is a carboxylic acid ester may be non-optimal for in vivo use (owing, for example, to their susceptibility to hydrolysis). However, such free acids, acid halides, and esters can be used as intermediates, for example, in the preparation of the corresponding amides.

In all of the formulae set forth in this document which contain one or more chiral centers and which do not specify the stereochemistry of a particular chiral center, such formulae are to be construed as referring each of all possible stereochemistries. Thus, for example, where a formula is shown as having two chiral centers C*$^A$ and C*$^B$, the formula is meant to include (i) compounds in which each of C*$^A$ and C*$^B$ is entirely in the R configuration, (ii) compounds in which each of C*$^A$ and C*$^B$ is entirely in the S configuration, (iii) compounds in which C*$^A$ is entirely in the S configuration and C*$^B$ is entirely in the R configuration, (iv) compounds in which C*$^A$ is entirely in the R configuration and of C*$^B$ is entirely in the S configuration, and (v) racemic and other mixtures of (i), (ii), (iii), and (iv). Illustratively, a compound having the formula:

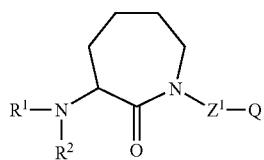

is meant to include compounds having any one of the following formulae:

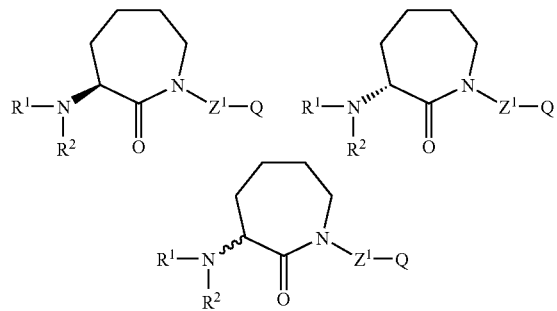

or mixtures thereof. By way of further illustration, a compound having the formula:

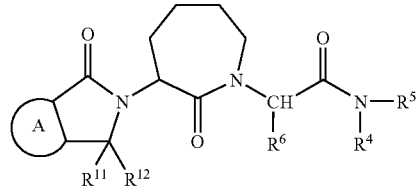

is meant to include compounds having any one of the following formulae:

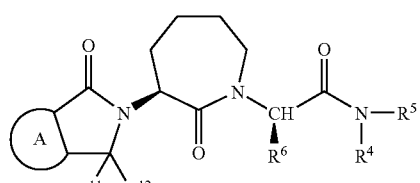

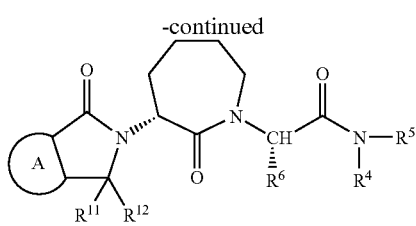
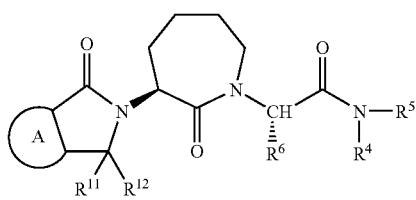
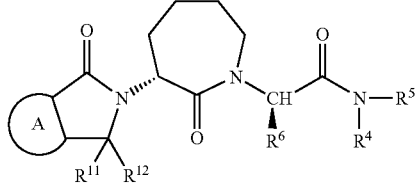
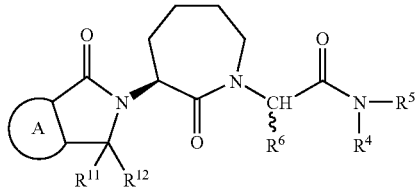
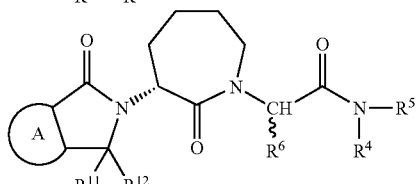
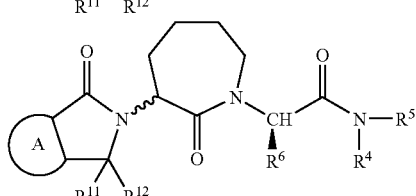
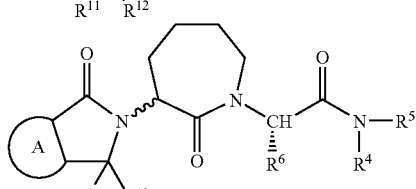
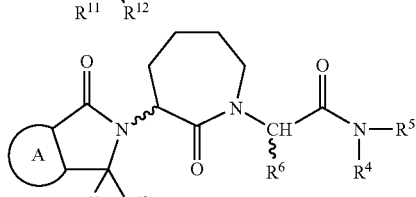

and mixtures thereof.

The present invention is further illustrated by the following non-limiting examples.

EXAMPLES

Example 1

Synthetic Procedures

Compounds 101 and 102 of the present invention were prepared in accordance with the following Scheme A.

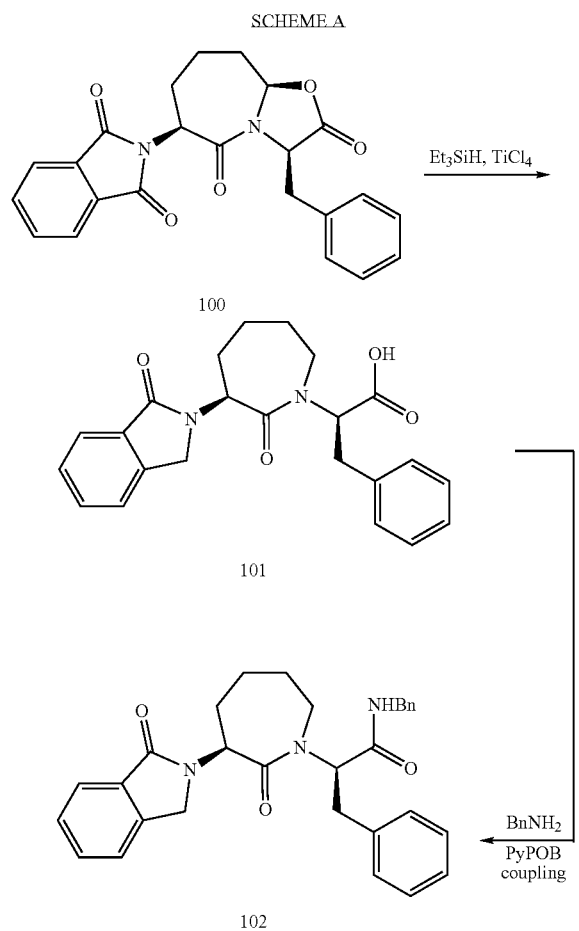

Briefly, (3R,6S,9aR)-3-benzyl-tetrahydro-6-(1,3-dioxo-isoindolin-2-yl)oxazolo[3,2-a]azepine-2,5(3H,6H)-dione (100) was prepared following the procedure set forth in Robl et al., "Peptidomimetic Synthesis: A Novel, Highly Stereoselective Route to Substituted Freidinger Lactams," *J. Am. Chem. Soc.*, 116:2348-2355 (1994), which is hereby incorporated by reference. NMR was in agreement with reported compound. $^1$H-NMR (CDCl$_3$) δ −0.15 (m, 1H), 1.61 (m, 1H), 1.71 (m, 1H), 1.85 (m, 2H), 2.57 (m, 1H), 3.25 (d, J=13.6 HZ, 1H), 3.58 (dd, J=13.6, 6.4 Hz, 1H), 4.67 (d, J=11.6 Hz, 1H), 4.71 (d, J=6.0 HZ, 1H), 5.57 (d, J=10.8 Hz, 1H), 7.23-7.42 (m, 5H), 7.73-7.98 (m, 2H).

2(R)-[2-Oxo-3(S)-(1-oxo-1,3-dihydro-isoindol-2-yl)-cycloheptyl]-3-phenyl-propionic acid (101) was prepared using the following procedure. Dione 101 (0.29 g, 0.7 mmole) was dissolved in 5 ml of anhydrous dichloromethane ("DCM"). Triethylsilane (1.13 ml, 7.0 mmole) and titanium tetrachloride (1.4 ml, 1M in DCM) were then added, and the mixture was then stirred at room temperature for 3 days. The reaction mixture was then quenched with water and extracted with ethyl acetate. The organic layer was washed with brine, dried with anhydrous sodium sulfate, and concentrated under vacuum. The residue was then purified using silica gel chromatography starting with ethyl acetate as an eluant followed by 2% acetic acid in ethyl acetate. The compound was collected as white solid (0.05 gm, 18%). $^1$H-NMR (CDCl$_3$) δ 1.46 (m, 1H), 1.68-1.97 (m, 5H), 2.90 (dd, J=16.0, 3.5 Hz, 1H), 3.22 (m, 1H), 3.36-3.43 (m, 2H), 4.34-5.00 (abq, J=17.0 Hz, 2H), 4.56 (m, 1H), 5.25 (d, J=11.0 Hz, 1H), 7.24-7.30 (m, 3H), 7.70 (t, J=7.5 Hz, 2H), 7.46 (t, J=7.5 Hz, 2H), 7.55 (t, J=7.5 Hz, 1H), 7.91 (d, J=7.5 Hz, 1H). MS (ES) m/z=391 (M-H)$^-$.

N-Benzyl-2(R)-[2-oxo-3(S)-(1-oxo-1,3-dihydro-isoindol-2-yl)-cycloheptyl]-3-phenyl-propionamide (102) was synthesized from acid 101 and benzyl amine following the general method for amide coupling. The product was obtained as a white solid. $^1$H-NMR (CDCl$_3$) δ 1.25 (m, 1H), 1.67-1.95 (m, 5H), 2.98 (dd, J=14.5, 8.0 Hz, 1H), 3.37-3.50 (m, 2H), 3.60 (m, 1H), 4.25-4.45 (dabq, J=12.0, 15.0 Hz, 2H) 4.32-4.86 (abq, J=16.5 Hz, 2H), 5.23 (d, J=10.5 Hz, 1H), 5.38 (t, J=8.0 Hz, 1H), 7.08 (d, J=7.5 Hz, 2H), 7.19-7.31 (m, 8H), 7.47 (m, 2H), 7.54 (m, 1H), 7.86 (d, J=7.5 Hz, 1H). (HRMS, ESI): m/z found 504.22595 [M+Na]$^+$, C$_{30}$H$_{31}$N$_3$O$_3$Na requires 504.2258.

Example 2

Effects of Compound 102 on Cancer Cell Growth Inhibition

Figure 1B:
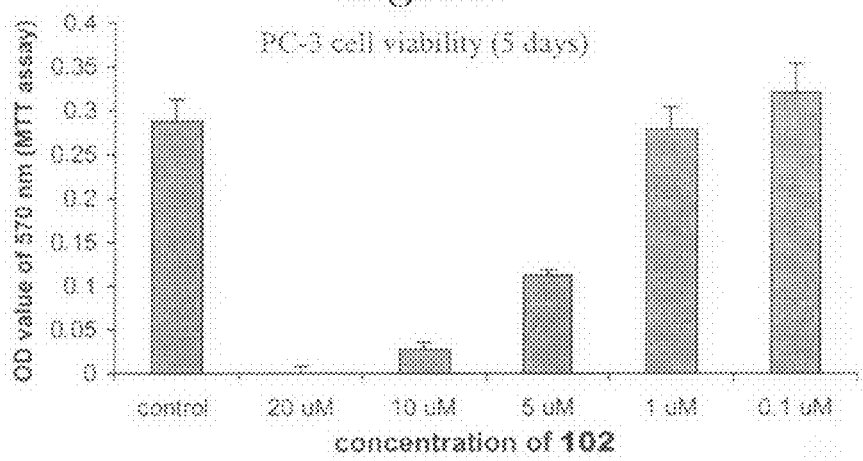
Figure 2A:
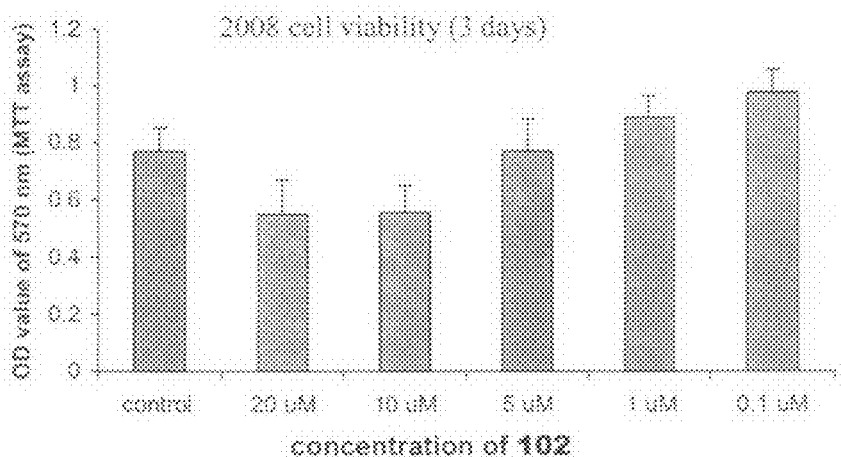
FIGS. 2A-2B are bar graphs showing the effect of a compound of the present invention on 2008 ovarian cancer cell growth inhibition after 3 days treatment (FIG. 2A) and 5 days treatment (FIG. 2B).
Figure 2B:
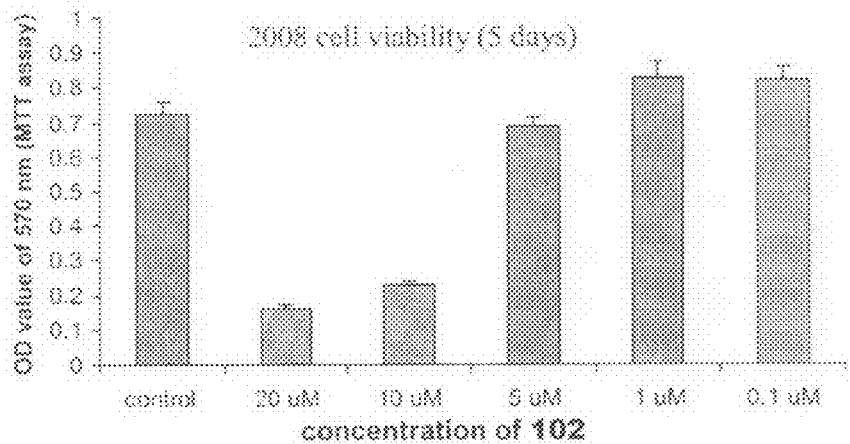
Figure 3A:
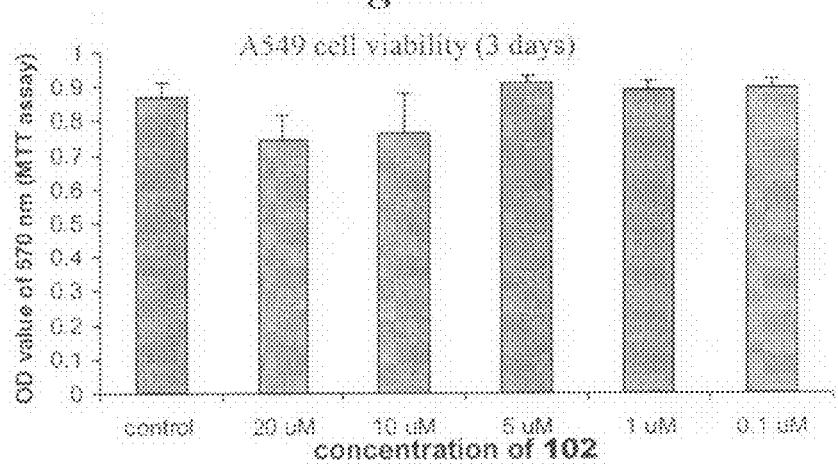
FIGS. 3A-3B are bar graphs showing the effect of a compound of the present invention on A549 lung cancer cell growth inhibition after 3 days treatment (FIG. 3A) and 5 days treatment (FIG. 3B).
Figure 3B:
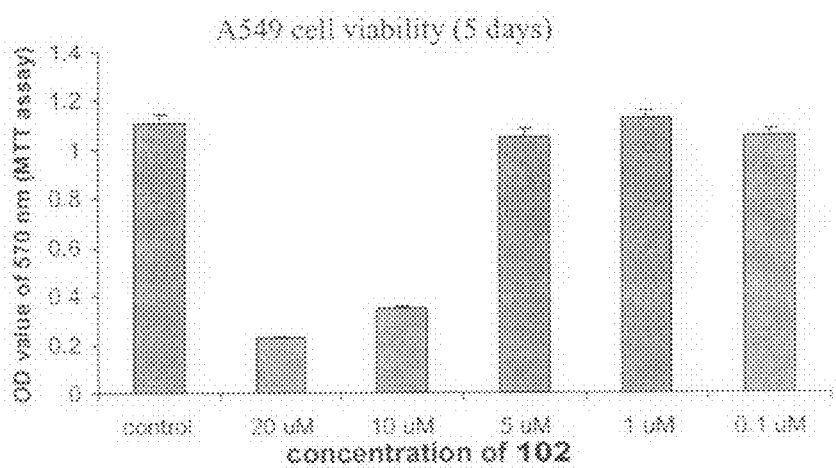

Functional screening of a drug library which included compound 102 by MTT assay following our previous protocol (Ling et al., "Differential Expression of Survivin-2B and Survivin-DeltaEx3 Is Inversely Associated with Disease Relapse and Patient Survival in Non-Small-Cell Lung Cancer (NSCLC)," *Lung Cancer*, 49:353-361 (2005), which is hereby incorporated by reference) resulted in the hit of compound 102. Compound 102 showed significant cell growth inhibition property in several cancer cell types, including PC-3 prostate cancer cells, 2008 ovarian cancer cells, and A549 lung cancer cells at initial concentration of 20 μM (data not shown). We then studied in detail the concentration-dependent effects of compound 102 on cell growth inhibition in various cancer cell types. FIGS. 1A and 1B show the results from PC-3 prostate cancer cells for 3 and 5 days after compound 102 treatment. Similar results were also obtained in MCF-7 breast cancer cells. FIGS. 2A and 2B show the results from 2008 ovarian cancer cells for 3 and 5 days after compound 102 treatment. FIGS. 3A and 3B show the results from A549 lung cancer cells for 3 and 5 days after compound 102 treatment.

From these results, we conclude that the compound 102 has broad and strong inhibitory effects on various cancer cell growth. However, the time course of its drug effect may vary among different cancer cell types.

Example 3

Effects of Compound 102 on Cancer Cell Colony Formation

Figure 4A:
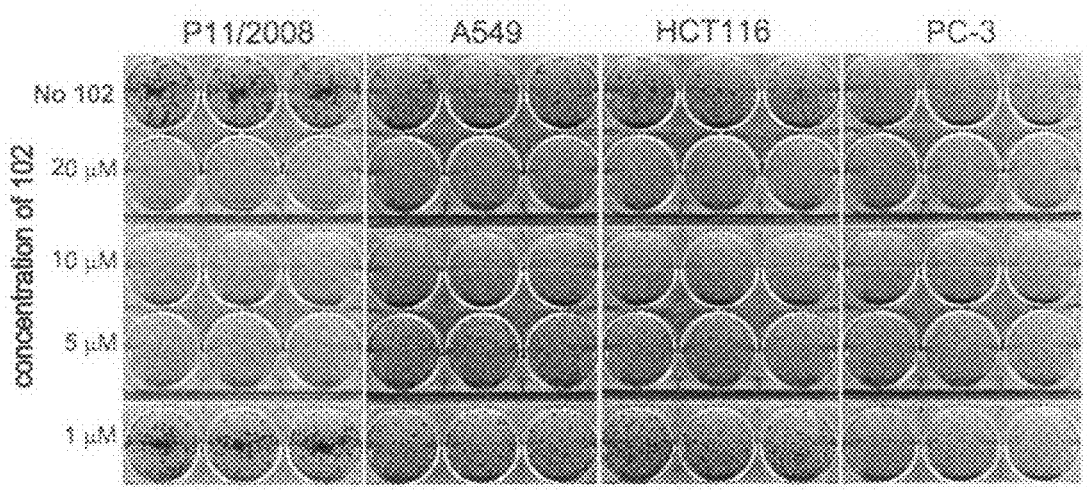
FIG. 4A is an image of a series of stained 6-well plates showing the effect of various concentrations (1 μM, 5 μM, 10 μM, and 20 μM) of a compound of the present invention and a control (no compound of the present invention) on colony formation for P11/2008 ovarian cancer cells, A549 lung cancer cells, HCT116 colon cancer cells, and PC-3 prostate cancer cells.
Figure 4B:
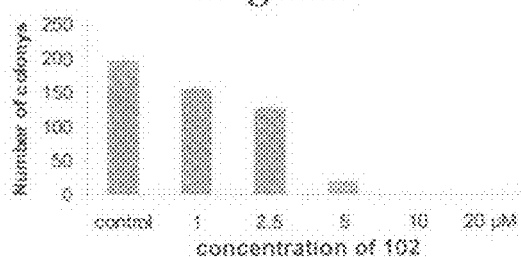
FIGS. 4B-4E are bar graphs showing quantitative results derived from the stained 6-well plates shown in FIG. 4A for P11/2008 ovarian cancer cells (FIG. 4B), A549 lung cancer cells (FIG. 4C), HCT116 colon cancer cells (FIG. 4D), and PC-3 prostate cancer cells (FIG. 4E).
Figure 4C:
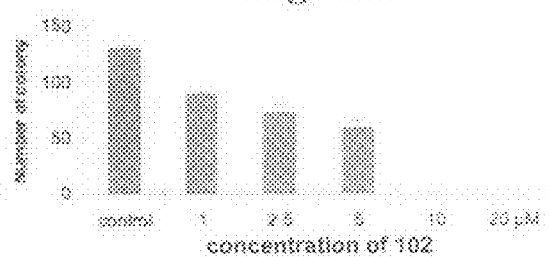
Figure 4D:
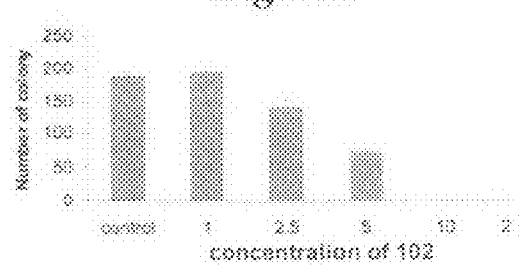
Figure 4E:
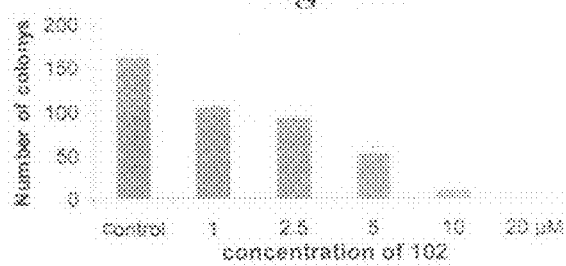

Next, we tested the inhibitory effect of compound 102 on cancer cell colony formation for various cancer cells (P11/208, A549, HCT116, and PC-3). Two hundred cells were seeded in each well of 6-well plates. Twenty-four hours after seeding, the cells were treated one time with compound 102 at various concentrations (0 µM, 20 µM, 10 µM, 5 µM, and 1 µM). The cells were then cultured for two weeks and stained with crystal violet to detect cancer colony formation. The results are presented in FIGS. 4A-4E. FIG. 4A is an image of the stained 6-well plates. FIG. 4B (P11/2008), FIG. 4C (A549), FIG. 4D (HCT116), and FIG. 4E (PC-3) are bar graphs showing quantitative results derived from the stained 6-well plates shown in FIG. 4A.

Example 4

Effects of Compound 102 on Cancer Cell Morphological Changes

Figure 5A:
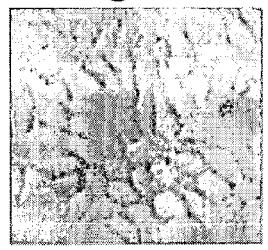
FIGS. 5A-5E are images showing the effect of a compound of the present invention on cancer cell morphology.
Figure 5B:
Figure 5C:
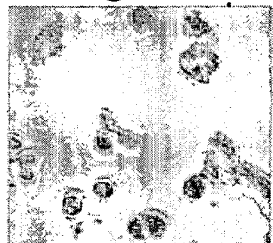
Figure 5D:
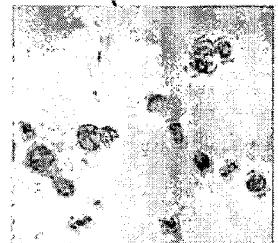
Figure 5E:
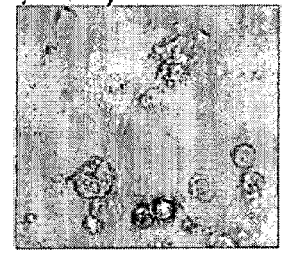

The effects of compound 102 on cancer cell morphological changes appeared to be very interesting. For example, treatment of various cancer cells with compound 102 at 20 µM for 24 hours did not show significantly morphological changes. The morphological changes began after 24-hour treatment, and dramatic changes were observed after 72-hour treatment. The results from the MCF-7 breast cancer cells after 3 days' treatment are shown in FIGS. 5A-5E. FIGS. 5C-5E are three images of MCF-7 breast cancer cells treated for 3 days with 20 µM of compound 102. FIGS. 5A-5B are control images (no compound 102). Similar results were also obtained in other cancer cells. Here, we would like to point out that the slow effect of compound 102 on cell morphological changes and cancer cell growth inhibition in certain cell type suggest that there is a unique drug action mechanism involved in the effects of compound 102 action.

Example 5

Effects of Compound 102 on Cancer Cell Cycle Control

Figure 6A:
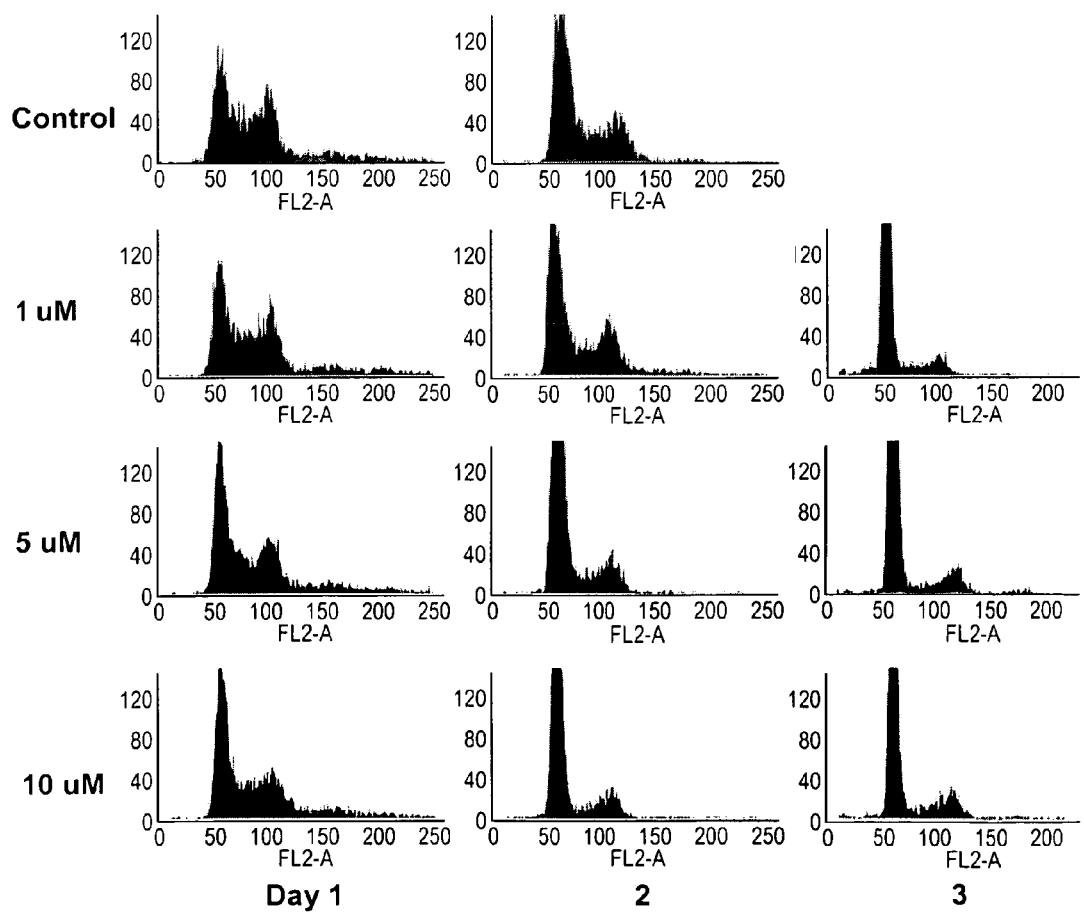
FIGS. 6A-6C are a series of histograms showing the effect of a compound of the present invention (at three concentrations (1 µM, 5 µM, and 10 µM) and control (no compound of the present invention)) on the cell cycle distribution after 1 day, 2 days, and 3 days treatment for 2008 ovarian cancer cells (FIG. 6A), lung cancer cells (FIG. 6B), and PC-3 prostate cancer cells (FIG. 6C).
Figure 6B:
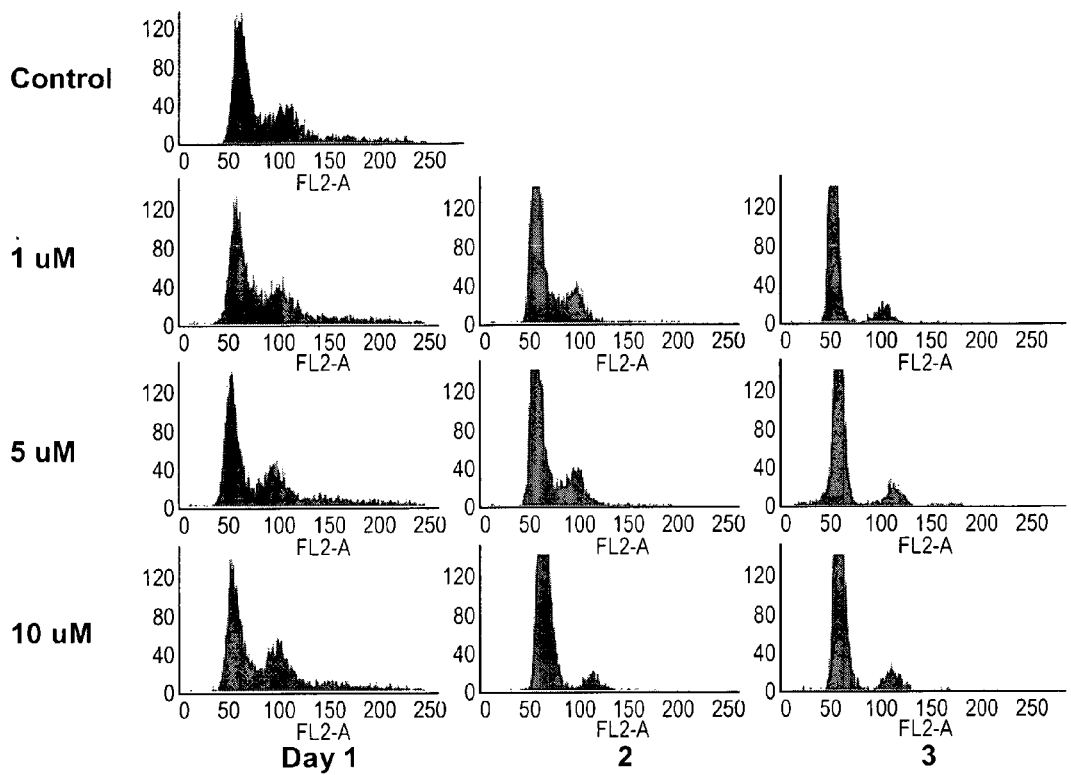
Figure 6C:
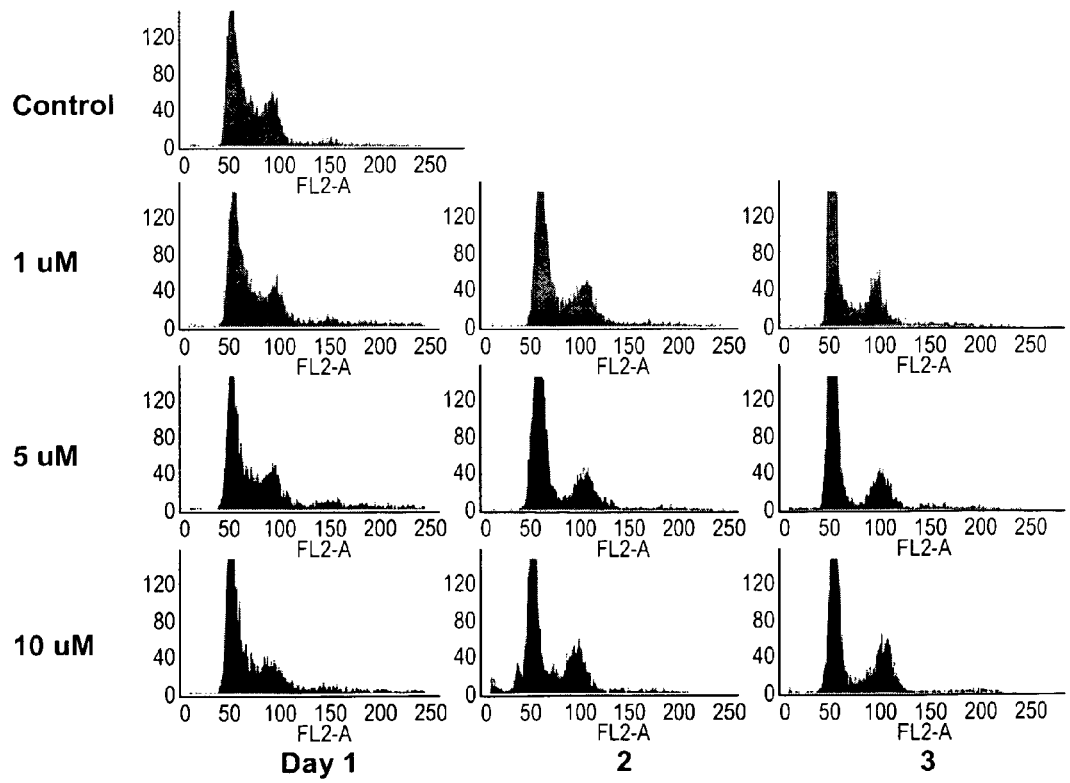

We next studied the effects of compound 102 on cancer cell cycle control. We found that compound 102 effectively arrests cancer cells in G1 phase of the cell cycle as shown in FIGS. 6A-6C. FIGS. 6A-6C show the effect of compound 102 (at three concentrations (1 µM, 5 µM, and 10 µM) and control (no compound 102)) on the cell cycle distribution after 1 day, 2 days, and 3 days treatment for 2008 ovarian cancer cells (FIG. 6A), lung cancer cells (FIG. 6B), and PC-3 prostate cancer cells (FIG. 6C). This observation is consistent with the observation below (Example 6) that p53 and p21 status is associated with cancer cell growth inhibition induced by compound 102.

Example 6

Effects of p53 and p21 Status in HCT116 Colon Cancer Cells on Cell Growth Inhibition Mediated by Compound 102

Figure 7:
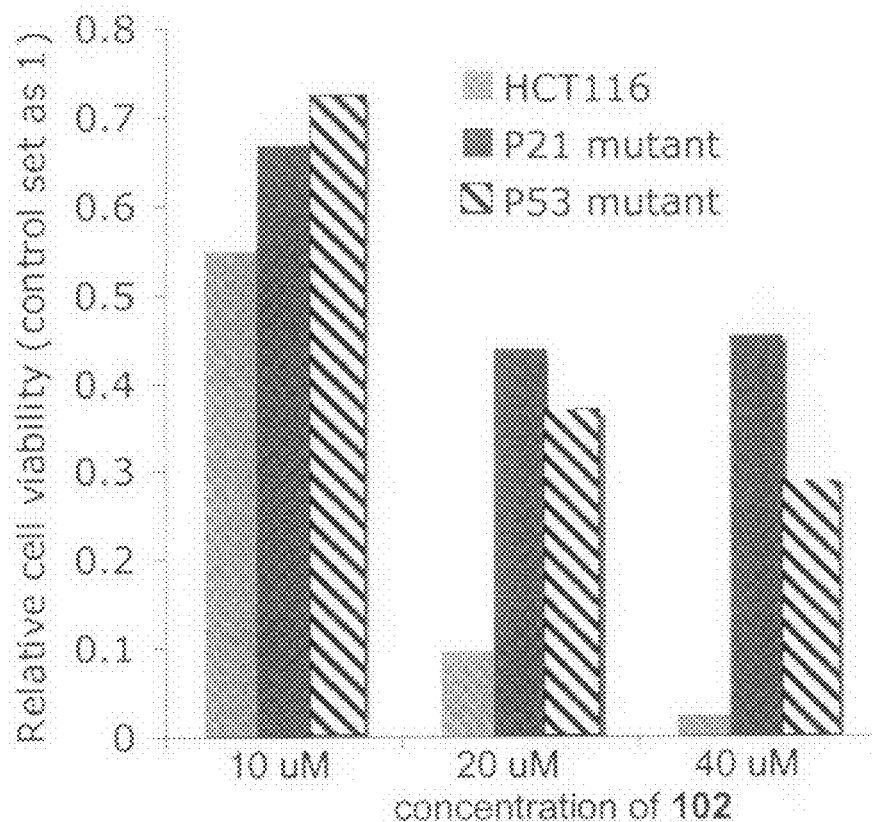
FIG. 7 is a bar graph showing the effects of p53 and p21 status in HCT116 colon cancer cells on cell growth inhibition mediated by a compound of the present invention.

Since the data suggested that compound 102 could induce cancer cell G1 arrest, we examined the effects of p53 and p21 status in HCT116 colon cancer cells on cell growth inhibition mediated by compound 102. The results are presented in FIG. 7 and indicate that, consistent with the factor that compound 102 promotes cancer cells G1 arrest, the efficacy of compound 102 on cancer cell growth inhibition is associated with both p53 and p21 gene status.

Example 7

Effect of Compound 102 on DNA Fragmentation and Caspase Activation

Figure 8:
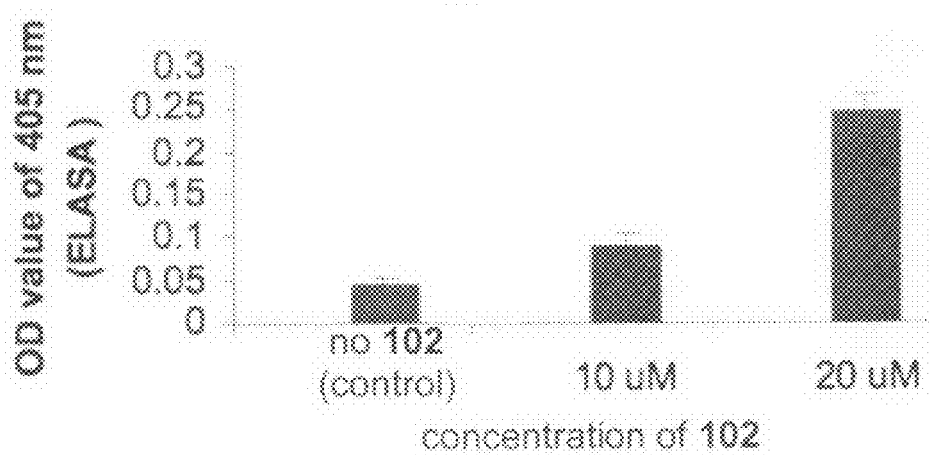
FIG. 8 is a bar graph showing the effect of a compound of the present invention on the cytoplasmic histone-associated DNA fragmentation at 48 hours after treatment in HCT116 colon cancer cells at 2 concentrations (10 µM and 20 µM) compared with control (no compound of the present invention).
Figure 9:
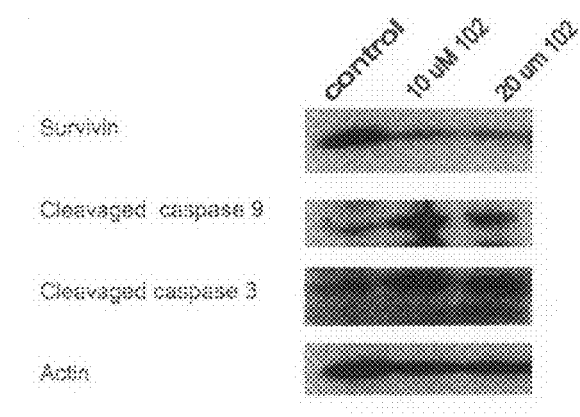
FIG. 9 is an image of a series of Western blots indicating that a compound of the present invention downregulates survivin expression and activates caspases 9 and 3 in HCT116 colon cancer cells at 48 hours after treatment.

To test whether compound 102 induces apoptotic cancer cell death, we performed DNA fragmentation cell death ELISA assays (Roche) and Western blots to test activation of caspases. FIG. 8 shows the effect of compound 102 on the cytoplasmic histone-associated DNA fragmentation at 48 hours after compound 102 treatment in HCT116 colon cancer cells at 2 concentrations (10 µM and 20 µM) compared with control (no compound 102). FIG. 8 demonstrates that compound 102 strikingly enhances cell DNA fragmentation, a hallmark of apoptotic cell death. FIG. 9 shows series of Western blots indicating that compound 102 downregulates survivin expression and activates caspases 9 and 3 in HCT116 colon cancer cells at 48 hours after compound 102 treatment.

Example 8

Figure 10:
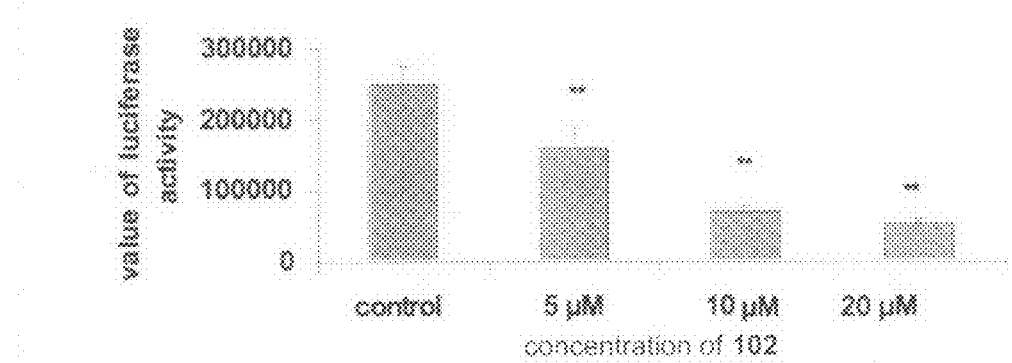
FIG. 10 is a bar graph showing that survivin promoter activity in MCF-7 breast cancer cells decreases with increasing concentration of a compound of the present invention. *p<0.05, **p<0.01.

Effect of Compound 102 on Survivin Expression, Promoter Activity and XIAP Expression As discussed in Example 7, FIG. 9 showed that activation of caspases 9 and 3 induced by compound 102 is associated with downregulation of survivin expression. Intriguingly, we further found that compound 102 is able to downregulate survivin promoter activity. Briefly, a survivin promoter-luciferase construct (pLuc-6309) was transfected into MCF-7 breast cancer cells. Transfected cells were treated with compound 102 (at 3 concentrations (5 µM, 10 µM, and 20 µM)) and control (no compound 102) for 24 hours at 12 hours after transfection. A luciferase activity assay was then performed using the Dual Luciferase Reporter Assay System (Promega). The results, presented in FIG. 10, show that survivin promoter activity decreases with increasing compound 102 concentration. These observations suggest the possibility that downregulation of survivin expression and promoter activity may be required for apoptosis induction.

Figure 11:
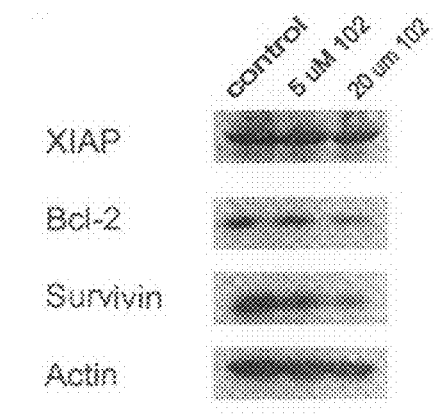
FIG. 11 is an image of a series of Western blots indicating that, while a compound of the present invention downregulates both survivin and Bcl-2 expression in 2008 ovarian cancer cells, it has no effect on the expression of XIAP in 2008 ovarian cancer cells.

To test the specificity of compound 102 on survivin inhibition, we performed Western blots to determine the effect of compound 102 on Bcl-2 expression and on XIAP expression. The results, presented in FIG. 11, show that while compound 102 downregulates both survivin and Bcl-2 expression in 2008 ovarian cancer cells, it has no effect on the expression of XIAP in 2008 ovarian cancer cells.

Although the invention has been described in detail for the purpose of illustration, it is understood that such detail is solely for that purpose, and variations can be made therein by those skilled in the art without departing from the spirit and scope of the invention which is defined by the claims that are set forth below.

What is claimed is:

1. A compound having the formula:

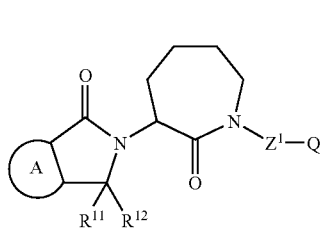

wherein $R^{11}$ and $R^{12}$ are the same or different and are selected from the group consisting of hydrogen, alkyl, and aryl; and wherein A represents a fused aryl ring; and wherein $Z^1$ is an alkylene moiety; Q is a carboxylic acid derivative.

2. A compound according to claim 1, wherein A represents a phenyl ring, and wherein each of $R^{11}$ and $R^{12}$ is a hydrogen atom.

3. A compound according to claim 1 having the formula:

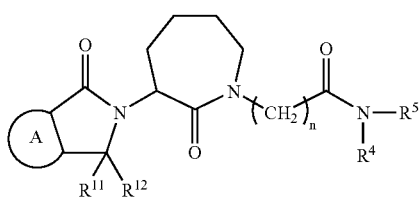

wherein A represents a fused aryl ring; wherein $R^{11}$ and $R^{12}$ are the same or different and are selected from the group consisting of hydrogen, alkyl, and aryl; wherein n is an integer from 1 to 4; and wherein $R^4$ and $R^5$ are the same or different and are selected from the group consisting of hydrogen, alkyl, and aryl or $R^4$ and $R^5$, taken together with the nitrogen atom to which they are bound, form a ring.

4. A compound according to claim 1 having the formula:

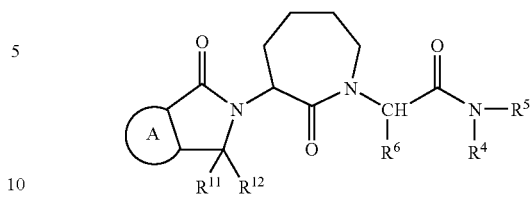

wherein A represents a fused aryl ring; wherein $R^{11}$ and $R^{12}$ are the same or different and are selected from the group consisting of hydrogen, alkyl, and aryl; wherein $R^4$ and $R^5$ are the same or different and are selected from the group consisting of hydrogen, alkyl, and aryl or $R^4$ and $R^5$, taken together with the nitrogen atom to which they are bound, form a ring; and $R^6$ is an alkyl group.

5. A compound according to claim 4, wherein $R^6$ is a benzyl group.

6. A compound according to claim 1 having the formula:

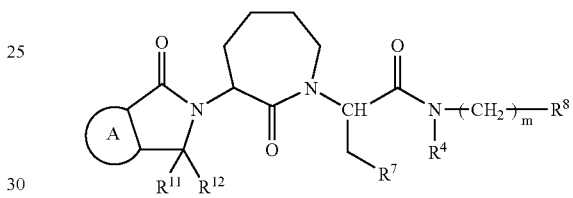

wherein A represents a fused aryl ring; wherein $R^{12}$ and $R^{12}$ are the same or different and are selected from the group consisting of hydrogen, alkyl, and aryl; wherein $R^7$ is an aryl group; $R^8$ is an aryl group; and m is 0, 1, 2, or 3.

7. A compound according to claim 6, wherein A represents a phenyl ring, and wherein each of $R^{11}$ and $R^{12}$ is a hydrogen atom.

8. A compound according to claim 6, wherein A represents a phenyl ring, each of $R^{11}$ and $R^{12}$ is a hydrogen atom, m is 1, $R^4$ is a hydrogen atom, $R^7$ is a phenyl group, and $R^8$ is a phenyl group.

* * * * *

UNITED STATES PATENT AND TRADEMARK OFFICE
CERTIFICATE OF CORRECTION

Page 1 of 1

PATENT NO.         : 7,968,708 B2
APPLICATION NO.    : 11/999723
DATED              : June 28, 2011
INVENTOR(S)        : Hangauer et al.

It is certified that error appears in the above-identified patent and that said Letters Patent is hereby corrected as shown below:

In the claims:

Column 26, line 32, claim 6 should read:

--$R^{11}$ and $R^{12}$--.

Signed and Sealed this
Third Day of April, 2012

David J. Kappos
*Director of the United States Patent and Trademark Office*